United States Patent
Rock (10) Patent No.: US 11,468,975 B2
(45) Date of Patent: Oct. 11, 2022

(54) MEDICATION RECONCILIATION SYSTEM AND METHOD

(71) Applicant: Vivify Health, Inc., Plano, TX (US)

(72) Inventor: Eric Lee Rock, Plano, TX (US)

(73) Assignee: VIVIFY HEALTH, INC., Plano, TX (US)

( * ) Notice: Subject to any disclaimer, the term of this patent is extended or adjusted under 35 U.S.C. 154(b) by 795 days.

(21) Appl. No.: 15/144,417

(22) Filed: May 2, 2016

(65) Prior Publication Data
US 2016/0246928 A1 Aug. 25, 2016

Related U.S. Application Data

(63) Continuation of application No. 14/223,747, filed on Mar. 24, 2014, now abandoned, which is a (Continued)

(51) Int. Cl.
*G16H 20/10* (2018.01)
*G16H 70/40* (2018.01)
*G16H 30/20* (2018.01)

(52) U.S. Cl.
CPC ............ *G16H 20/10* (2018.01); *G16H 30/20* (2018.01); *G16H 70/40* (2018.01)

(58) Field of Classification Search
CPC ........ G16H 10/00; G16H 10/60; G16H 15/00; G16H 20/10; G16H 50/70; G16H 70/40;
(Continued)

(56) References Cited

U.S. PATENT DOCUMENTS

| 5,940,801 A | 8/1999 | Brown |
| 7,593,952 B2 | 9/2009 | Soll et al. |

(Continued)

FOREIGN PATENT DOCUMENTS

| WO | WO-2012056317 A2 * | 5/2012 | ............... A61J 7/00 |
| WO | WO-2012154637 A1 * | 11/2012 | ............. G16H 20/10 |
| WO | WO 2013033655 A1 | 3/2013 | |

OTHER PUBLICATIONS

Lee et al., Pill-ID: Matching and retrieval of drug pill images, May 1, 2012, Pattern Recognition Letters, vol. 33, Iss. 7, pp. 904-910. (Year: 2012).*

(Continued)

*Primary Examiner* — Christopher L Gilligan
(74) *Attorney, Agent, or Firm* — Shumaker & Sieffert, P.A.

(57) ABSTRACT

A system and method to determine and reconcile medication provided to a patient is disclosed. The system and method collect a medication image file (MIF) of a patient medication collection (PMC) using a mobile user device (MUD) and pill source imager (PSI). The MUD transmits the MIF to a host computer system (HSC) via a computer communication network (CCN). The HSC isolates individual MIF medication image elements (MIE) and compares each MIE against a pill image database (PID) to generate a potential pill match (PPM) list. The PPM is filtered and prioritized to produce a prioritized medication list (PML) using data from a pill correlation database (PCD), patient history database (PHD), and medical reading database (MRD). The PML describes probable PPM associations with specific known medications. A HCS graphical user interface (GUI) permits validation of each MIE/PML pair to produce a patient reconciled validated medication list (VML).

21 Claims, 8 Drawing Sheets

Related U.S. Application Data continuation-in-part of application No. 14/223,537, filed on Mar. 24, 2014, now Pat. No. 9,619,849.

(60) Provisional application No. 61/805,355, filed on Mar. 26, 2013.

(58) Field of Classification Search
CPC ........ G16H 30/20; G16H 20/00; G16H 30/00; G16H 30/40; G16H 70/00
See application file for complete search history.

(56) References Cited

U.S. PATENT DOCUMENTS

| | | | |
|---|---|---|---|
| 7,739,126 B1 | 6/2010 | Cave et al. | |
| 8,183,998 B2 | 5/2012 | Rao et al. | |
| 8,239,903 B1 | 8/2012 | Campagna et al. | |
| 8,301,233 B2 | 10/2012 | Zhang et al. | |
| 8,321,808 B2 | 11/2012 | Goetz et al. | |
| 8,326,651 B2 | 12/2012 | McLaren et al. | |
| 8,396,804 B1 | 3/2013 | Dala et al. | |
| 9,031,853 B2* | 5/2015 | Bartfeld | G06Q 40/08 705/2 |
| 9,361,562 B1* | 6/2016 | Hanina | G06K 7/1408 |
| 2002/0184055 A1 | 12/2002 | Naghavi et al. | |
| 2002/0184200 A1 | 12/2002 | Naghavi et al. | |
| 2003/0022141 A1 | 1/2003 | Packard | |
| 2004/0039254 A1 | 2/2004 | Stivoric et al. | |
| 2004/0102931 A1 | 5/2004 | Ellis et al. | |
| 2005/0102160 A1 | 5/2005 | Brown | |
| 2005/0283385 A1 | 12/2005 | Hunkeler et al. | |
| 2006/0030890 A1 | 2/2006 | Cosentino et al. | |
| 2006/0122469 A1 | 6/2006 | Martel | |
| 2006/0234202 A1 | 10/2006 | Brown | |
| 2007/0006322 A1 | 1/2007 | Karimzadeh et al. | |
| 2007/0015974 A1 | 1/2007 | Higgins et al. | |
| 2007/0116036 A1 | 5/2007 | Moore | |
| 2007/0191070 A1 | 8/2007 | Rao | |
| 2007/0198653 A1* | 8/2007 | Jarnagin | G16B 50/00 709/217 |
| 2007/0255345 A1 | 11/2007 | Krause | |
| 2008/0077436 A1 | 3/2008 | Muradia | |
| 2008/0242947 A1 | 10/2008 | Jung et al. | |
| 2008/0275317 A1 | 11/2008 | Cho et al. | |
| 2008/0281633 A1 | 11/2008 | Burdea et al. | |
| 2009/0012818 A1* | 1/2009 | Rodgers | G06F 19/3462 705/3 |
| 2009/0150416 A1 | 6/2009 | Baker et al. | |
| 2011/0029327 A1 | 2/2011 | Dunlop | |
| 2011/0166884 A1 | 7/2011 | Lesselroth et al. | |
| 2011/0234409 A1 | 9/2011 | Soliman | |
| 2011/0238435 A1 | 9/2011 | Rapaport et al. | |
| 2011/0295621 A1 | 12/2011 | Farooq et al. | |
| 2012/0041771 A1 | 2/2012 | Cosentino et al. | |
| 2012/0041783 A1* | 2/2012 | McKee | G06Q 50/24 705/3 |
| 2012/0183941 A1 | 7/2012 | Steinmetz | |
| 2012/0203573 A1 | 8/2012 | Mayer et al. | |
| 2012/0330684 A1* | 12/2012 | Jacobs | H04N 7/18 705/3 |
| 2013/0035955 A1 | 2/2013 | Torres | |
| 2013/0117044 A1* | 5/2013 | Kalamas | G06Q 50/24 705/3 |
| 2013/0138450 A1 | 5/2013 | Vigneux | |
| 2013/0176790 A1 | 7/2013 | Nguyen et al. | |
| 2013/0221082 A1* | 8/2013 | Botten | G06F 16/00 235/375 |
| 2013/0238360 A1* | 9/2013 | Bhathal | G16H 10/60 705/3 |
| 2013/0262155 A1 | 10/2013 | Hinkamp | |
| 2013/0329058 A1 | 12/2013 | Brossette et al. | |
| 2013/0339060 A1 | 12/2013 | Delaney et al. | |
| 2016/0006946 A1 | 1/2016 | Cohen et al. | |
| 2016/0114925 A1* | 4/2016 | Yuyama | G06K 9/46 382/141 |

OTHER PUBLICATIONS

Doukas, et. al., "Mobile Healthcare Information management Utilizing Cloud Computing and Android OS"; 32nd Annual International Conference of the IEEE EMBS Buenos Aires, Argentina, Aug. 31-Sep. 4, 2010.

* cited by examiner

MEDICATION RECONCILIATION SYSTEM AND METHOD

CROSS REFERENCE TO RELATED APPLICATIONS

This application is a continuation of U.S. application Ser. No. 14/223,747, filed Mar. 24, 2014, which is a continuation-in-part of U.S. application Ser. No. 14/223,537, filed Mar. 24, 2014, which claims the benefit of U.S. Provisional Application No. 61/805,355, filed Mar. 26, 2013, and this application also claims the benefit of U.S. Provisional Application No. 61/805,355, filed Mar. 26, 2013, the disclosures of each of the above are fully incorporated herein by reference.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for automated identification of patient medications and specifically for the identification of pills and/or capsules in which patient drugs/medications are delivered. Without limiting the scope of the present invention, the present invention may be advantageously applied to the following U.S. Patent Classifications: 348/207.1; 382/165; and 348/E05.024.

PRIOR ART AND BACKGROUND OF THE INVENTION

Prior Art System Context

Within the context of automated healthcare delivery systems there is often a need for healthcare professionals to determine an inventory of the medications that a patient may be taking at a particular time. This vital part of the patient medical history is often not available in any hardcopy or electronic form but must be manually determined by inspecting the medications, pills, capsules, drugs, pill bottles, prescriptions, and other items evidencing medication consumption. This manual process is time consuming and must be repeated often by several different healthcare providers to ensure that the patient is taking the proper complement of medication at any given time.

Furthermore, a medication reconciliation operation may need to be performed on a daily basis for a patient to ensure that each and every day the correct medications are properly administered. A manual medication reconciliation process in this situation is both expensive and in many cased impractical to implement for patients that are located at a distance from their healthcare providers.

Deficiencies in the Prior Art

The prior art as detailed above suffers from the following deficiencies:

Prior art medication reconciliation systems and methods do not permit automated identification of medications or other items evidencing medication identification.

Prior art medication reconciliation systems and methods do not utilize patient medical history as a basis for medication identification.

Prior art medication reconciliation systems and methods do not utilize relationships between medications as a basis for medication identification.

Prior art medication reconciliation systems and methods do not utilize patient medical readings as a basis for medication identification.

Prior art medication reconciliation systems and methods do not integrate medication reconciliation with patient history information.

Prior art medication reconciliation systems and methods do not integrate medication reconciliation into an overall automated patient healthcare plan (PHP).

While some of the prior art may teach some solutions to several of these problems, the core issue of identifying a random set of patient medications and integrating this information into a unified patient healthcare plan (PHP) has not been solved by the prior art.

OBJECTIVES OF THE INVENTION

Accordingly, the objectives of the present invention are (among others) to circumvent the deficiencies in the prior art and affect the following objectives in the context of a medication reconciliation system and method:

(1) Provide for a medication reconciliation system and method that permits automated identification of medications or other items evidencing medication identification.

(2) Provide for a medication reconciliation system and method that utilizes patient medical history as a basis for medication identification.

(3) Provide for a medication reconciliation system and method that utilizes relationships between medications as a basis for medication identification.

(4) Provide for a medication reconciliation system and method that utilizes patient medical readings as a basis for medication identification.

(5) Provide for a medication reconciliation system and method that integrates medication reconciliation with patient history information.

(6) Provide for a medication reconciliation system and method that integrates medication reconciliation into an overall automated patient healthcare plan (PHP).

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention covers the reconciliation of patient medications using an automated system incorporating OCR information retrieved from the pill bottle, barcode information retrieved from the pill bottle (or other source), visual pictures of the pills themselves, or other indicia of medication ingestion by the patient. This information is then matched to information in a pill database (online Physician's Desk Reference, etc.) and/or patient history. By properly interpreting the information taken from the patient interface (mobile phone, tablet, etc.) when used in conjunction with known medication data and the patient medical history this additional information can then be used to heuristically determine the patient medication complement and "fill in the gaps" if necessary in situations where the patient has failed to provide full information but has a medical history indicating additional medication is probably being used by the patient.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a MEDICATION RECONCILIATION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Medication Nomenclature not Limitive

The present invention may reference medication as a generic term to cover a wide range of functionally equivalent structures that may include pills, capsules, tablets, caplets, and other forms of medication delivery.

Medication Form not Limitive

The present invention may make use of a variety of medication identifiers to uniquely identify a particular medication image element (MIE) of a captured medication image file (MIF). This may include but is not limited to medication shape, size, color, imprint, scoring, and/or patterning.

Image Capture Scope not Limitive

The medication image file (MIF) used to observe and collect information on a patient medication collection (PMC) using a mobile user device (MUD) and pill source imager (PSI) may incorporate a broad range of information on the PMC, including but not limited to: medications, pill bottles, bar codes, RFID tags, prescriptions, medication documentation, patient history forms, and other indicia of medication ingested by the patient.

System Overview (0100)

Figure 1:
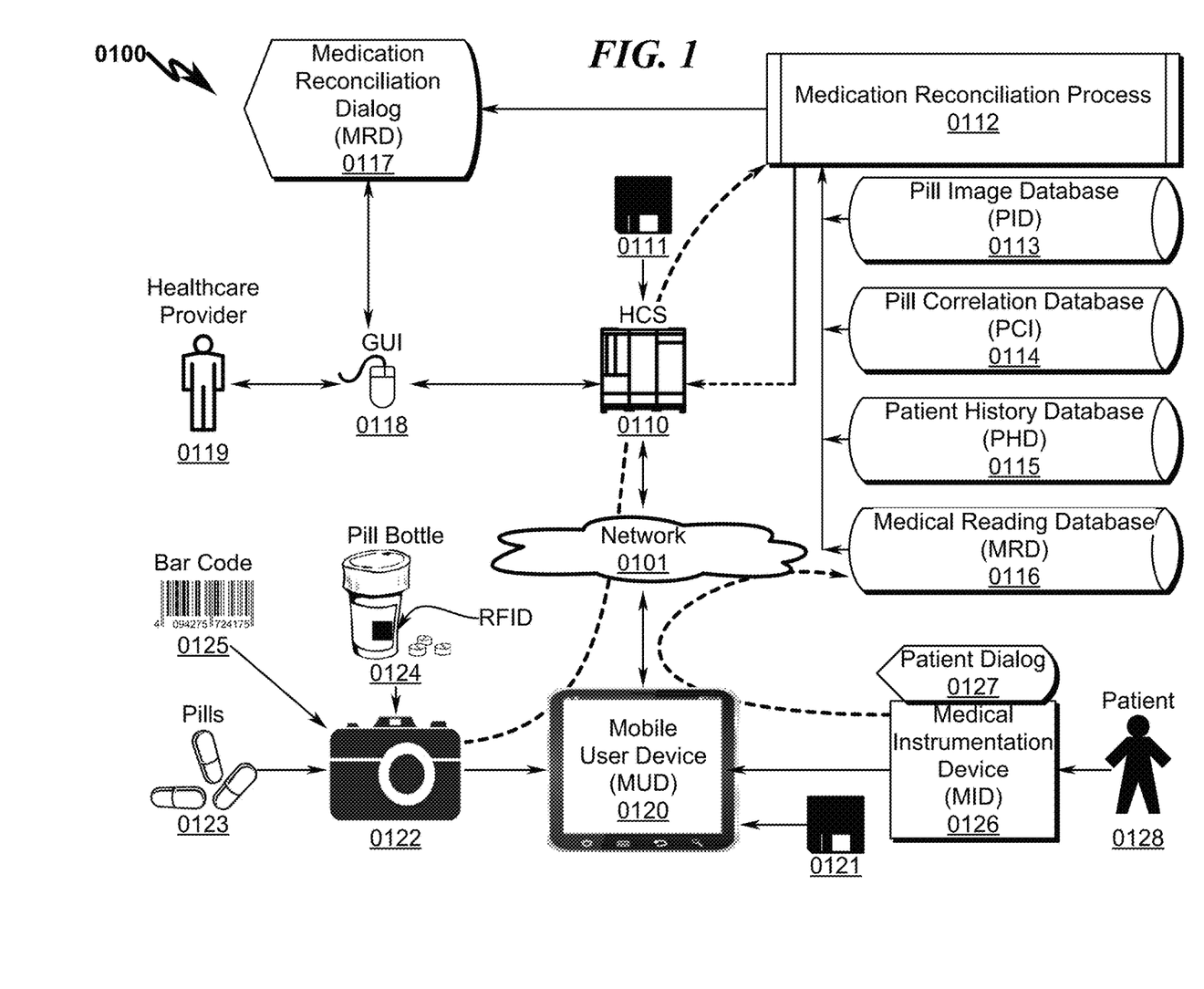
FIG. 1 illustrates an exemplary medication reconciliation system context.

The present invention may be summarized as depicted in the system block diagram of FIG. 1 (0100), and is comprised of two cooperating computer systems as depicted by the host computer system (HCS) (0110) and mobile user device (MUD) (0120). Each of these computer systems operates under control of machine instructions read from computer readable medium (0111, 0121). Within this context the host computer system (HCS) (0110) operates a medication reconciliation process (MRP) (0112) configured to interact with a pill image database (PID) (0113), pill correlation database (PCD) (0114), patient history database (PHD) (0115), and medical reading database (MRD) (0116). These databases (0113, 0114, 0115, 0116) operate to collect the following information:

Pill Image Database (PID) (0113)—This database contains images of known pill types (as may be extracted from a Physician's Desk Reference (PDR) and other sources) and identifying information on these pills including medication/drug name, generic equivalents, dosage, and approved disease treatment protocols. This information can be used by the MRP (0112) to determine a potential pill match (PPM) for an imaged pill/capsule. The list of PPMs for a given identified pill/capsule can then be used by the MRP (0112) with other data to further narrow the possibilities for identifying the individual pill/capsule. The PHD (0113) may be created from existing knowledge of medications and/or integrated with existing medication databases available from government agencies.

Pill Correlation Database (PCD) (0114)—This database correlates individual pills into groups that are related to specific disease treatments and groups including related disease treatments. For example, a group may be created for HEART DISEASE that includes only medications related to the treatment of heart disease. As an example of cross-disease groups, a group could be created for medications/drugs that are often applied to the treatment of DIABETES and KIDNEY FAILURE as they are often related in a given patient. This database can be used to aid in identifying pills that may be located by the imaging system but which may have several possible identification matches. The PCD (0114) may also incorporate data describing contraindicated medication combinations to provide a basis for warning healthcare professionals that a particular medication combination detected in the patient medication collection (PMC) poses a danger to the patient.

Patient History Database (PHD) (0115)—This database contains the patient medical history and diagnosed diseases (predefined coded diagnoses using the International Classification of Diseases (ICD) or hospital-specific Diagnosis-Related Group (DRG)). This information may be used by the MRP (0112) to filter the PPM to determine which pills/capsules are applicable to a given patient. Note that this PHD (0115) information may include information retrieved in real-time from a number of disparate electronic medical record (EMR) databases that may be drawn from hospitals, clinics, healthcare providers, and other sources of patient medical information.

Medical Reading Database (MRD) (0116)—This database contains patient (0128) medical readings that are obtained in real-time from a remote mobile user device (MUD) (0120) in conjunction with a medical instrumentation device (MID) (0126) and/or dialog data (0127) obtained from the patient (0128). This information is used by the MRP (0112) to categorize potential patient medical conditions that may be used by the MRP (0112) to filter the PPM to determine which pills/capsules are applicable to a given patient. For example, patient weight readings may be used as an aid to determine the potential for heart disease, diabetes, etc. and patient (0128) input dialogs (0127) may positively indicate a patient (0128) statement that they have a specific medical condition.

The MRP (0112) operating under control of the HCS (0110) is configured to present a medication reconciliation dialog (MRD) via a graphical user interface (GUI) (0118) to a healthcare provider (0119) that presents a graphical image of patient pills/capsules with labels indicating positively identified pills/capsules and prioritized labels indicating the probabilities of unknown pills being of a particular medication/drug.

Collection of the pill/capsule images operates as follows. A request for pill/capsule imaging is sent from the HCS (0110) to the MUD (0120) via a computer communication network (CCN) (0101) (typically the Internet) that requests that the patient (0128) image his/her complement of medications. The patient (0128) then uses a camera (0122) (which may be integrated within the MUD (0120)) to capture one or more images of pills/capsules (0123), pill/capsule bottles (0124) (which may include RFID tags), and/or bar codes (0125) (which may be located on pill/capsule bottles or on other patient prescription documentation) associated with his/her medications. This imaged information is then relayed by the MUD (0120) through the CCN (0101) to the HCS (0110) for match processing by the MRP (0112).

In addition to the imaging process described above, the patient (0128) may be connected to one or more medical instrumentation devices (MIDs) (0126) that collect medical data on the patient (0128) and transmit this through the MUD (0120) via the CCN (0101) to the MRD (0116). This real-time medical patient data may be used as a further discriminator by the MRP (0112) to determine the pill/capsule complement being consumed by the patient (0128).

Method Overview (0200)

Figure 2:
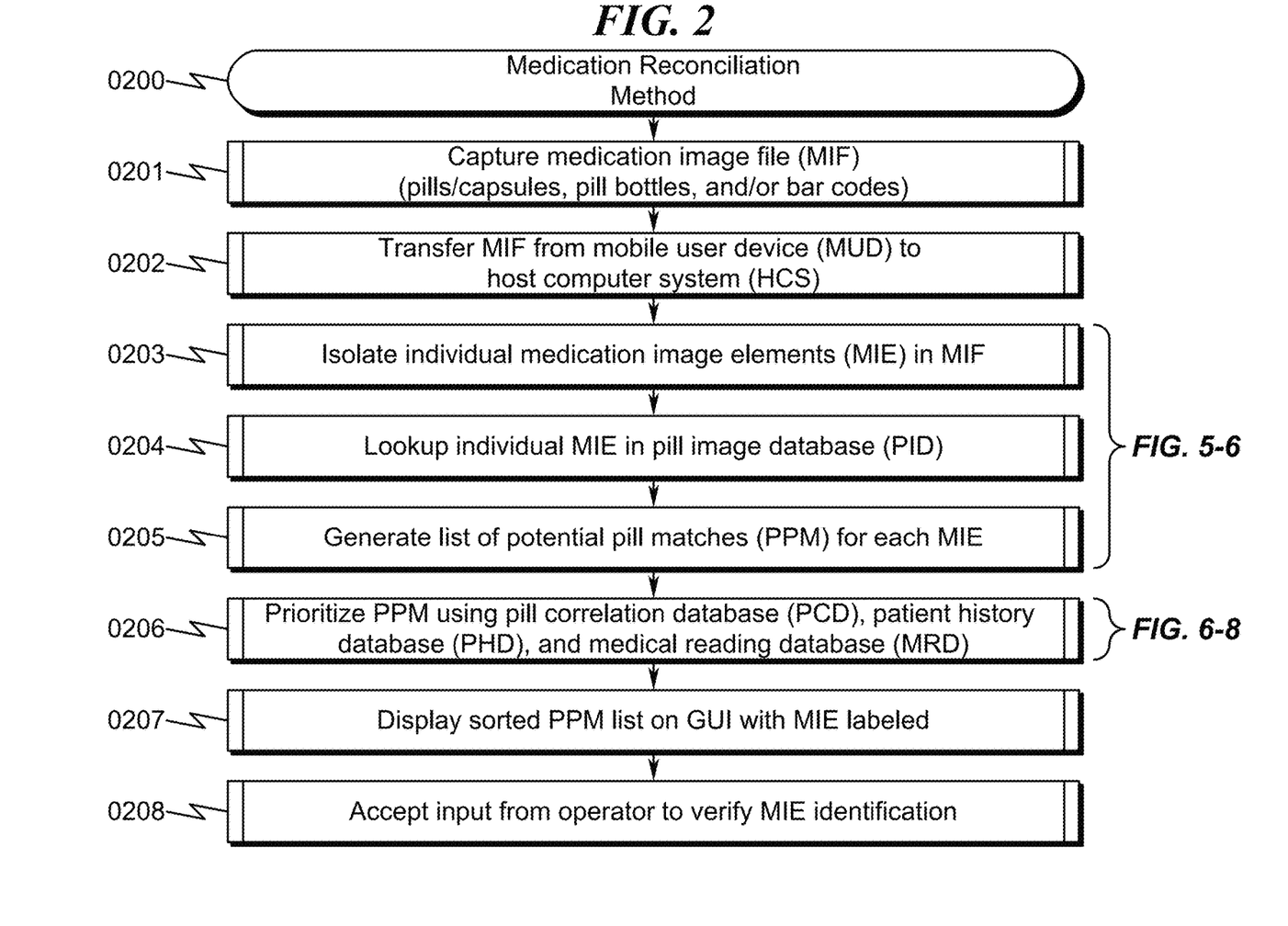
FIG. 2 illustrates a flowchart depicting an exemplary medication reconciliation method.

The system context as depicted in FIG. 1 (0100) is typically associated with a methodology as depicted in FIG. 2 (0200) and involves the following steps:
(1) with the MUD, capturing a medication image file (MIF) comprising pills/capsules, pill bottles, and/or bar codes (0201);
(2) with the MUD, transferring the MIF to the HCS (0202);
(3) with the HCS, isolating individual medical image elements (MIE) in the MIF (0203);
(4) with the HCS, identifying individual MIE within the pill image database (PID) (0204);
(5) with the HCS, generating a list of potential pill matches (PPM) for each MIE isolated (0205);
(6) with the HCS, prioritize the PPM using information extracted from a pill correlation database (PCD), patient history database (PHD), and medical reading database (MRD) (which may include patient query/response dialog (QRD) data) (0206);
(7) with the HCS, displaying a sorted PPM list on an operator GUI with MIE labeled (this display may also include patient history data (PHD) information from an EMR database to indicate the medications currently associated with the patient) (0207); and
(8) with the HCS, accepting input from the operator to verify MIE identification labels (0208).

Note that data contained within the MRD may be collected and updated in real-time from a medical instrumentation device (MID) communicating with the MUD.

System Embodiment Detail (0300)

Figure 3:
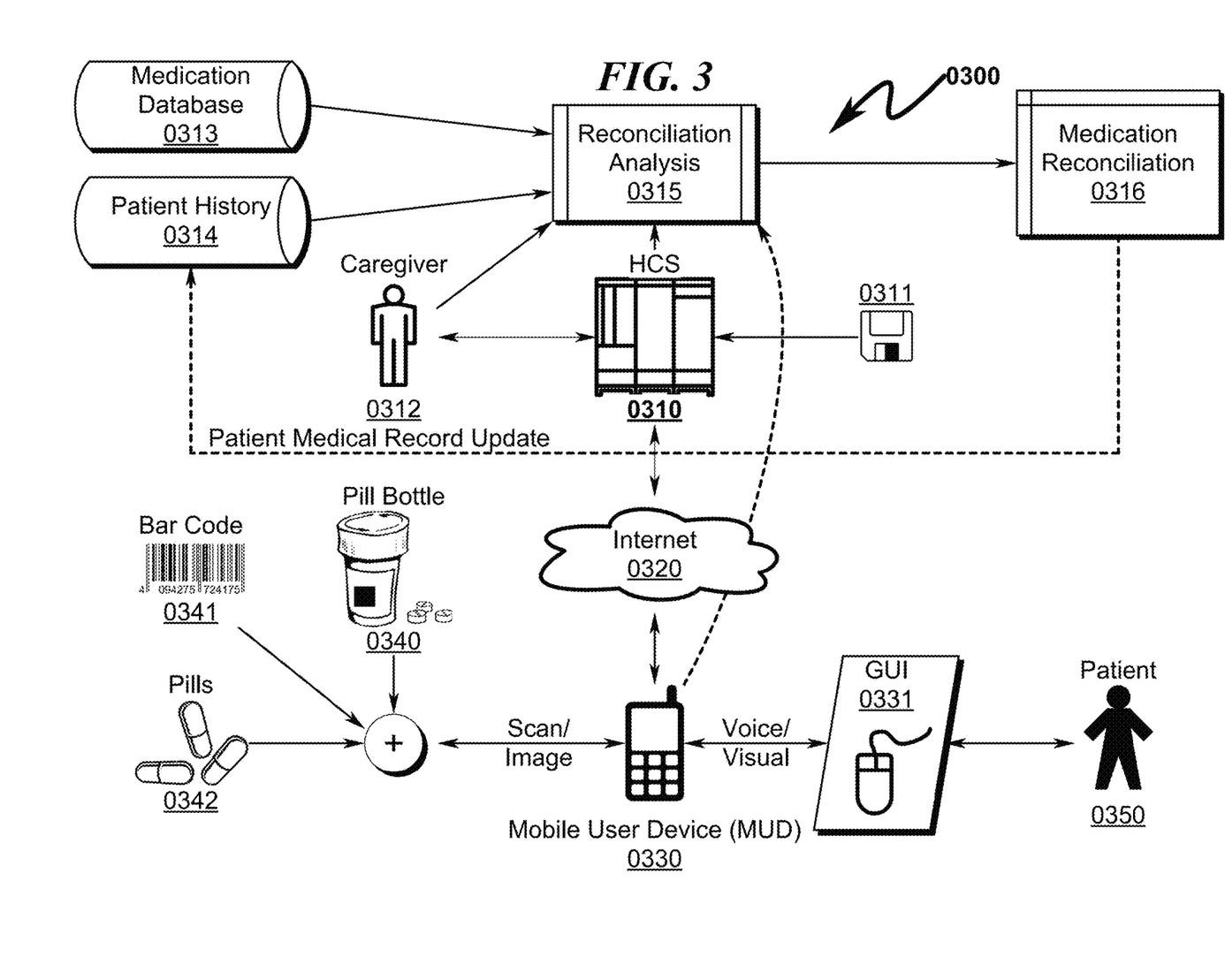
FIG. 3 illustrates a preferred exemplary detail block diagram of a preferred exemplary system embodiment of the present invention.

Additional detail of a preferred system embodiment is depicted in the system block diagram of FIG. 3 (0300), wherein the medication reconciliation system comprises:
(a) host computer system (HCS) (0310);
(b) computer communication network (CCN) (0320);
(c) mobile user device (MUD) (0330); and
(d) pill image database (PID) (0313); and
(e) patient history database (PHD) (0314).

In this hardware context the HCS (0310) is configured to communicate with the MUD through the computer communication network (0320). The HCS may be configured to perform at least one of the following:
  Scan the label (0340) of a prescription container and transfer the scanned/imaged label to said HCS.
  Scan the bar code (0341) of a prescription container and transfer the scanned/imaged bar code to the HCS.
  Photograph pills/capsules/tablets (0342) associated with the prescription container and transfer the pill photographs to the HCS.
  Collect RFID tag information from pills/capsules/tablets (0342) associated with the prescription container and transfer the RFID information to the HCS.

The HCS is configured to identify the pills using a reconciliation analysis process (0315) by converting text contained in the scanned/imaged label, interpreting the scanned/imaged bar code, and matching the pill photographs with information retrieved from the PID. Once the pills are identified the HCS is configured to store the pill identification in a medication reconciliation data structure (MRD). The MRD is configured to coordinate interaction between a graphical user interface (GUI) servicing a caregiver and an audio/visual interface (0331) operating under control of the MUD servicing a patient. The HCS (0310) is configured to update the PHD (0314) with the MRD based on said interaction between the caregiver and the patient.

Potential Pill Match (PPM) List Creation Method (0400)-(0500)

Associated with the exemplary system overview described in above is a potential pill match (PPM) list creation method that is used to take the medication image file (MIF) and extract information regarding various medications that the patient may be consuming. Note that the MIF may contain a variety of pieces of visual information that includes but is not limited to: pill/capsule/tablet/caplet outlines, pill bottle images, prescription images, bar codes, prescriptions, and other information supporting the patient medication collection (PMC). Thus, the task of identifying patient medications in this context spans that of pill/capsule/tablet/caplet visual identification and extends to a variety of other visual cues.

To solve this complex problem the present invention first captures a medication image file (MIF) of a scene that may include a variety of patient medication collection (PMC) cues. This MIF is then fractured into individual medication image elements (MIEs) that are associated with an individual cue such as a pill, prescription, bar code, etc. Once the MIE has been identified, information on the MIE can be extracted to search against a pill image database (PID) that contains image matching information on pills as well as other information on medications such as text names that might be associated with a pill bottle, prescription, or bar code. This search of the MIE decoded information against the PID may result in multiple matches, all of which are retained in a potential pill match (PPM) list associated with the MIE. The PPM is then processed further against contextual information about the patient, medications that are related to one another, medications that are related to specific diseases, and real-time patient monitoring data to rank the PPM list as to the most probable medication complement for the patient.

Figure 4:
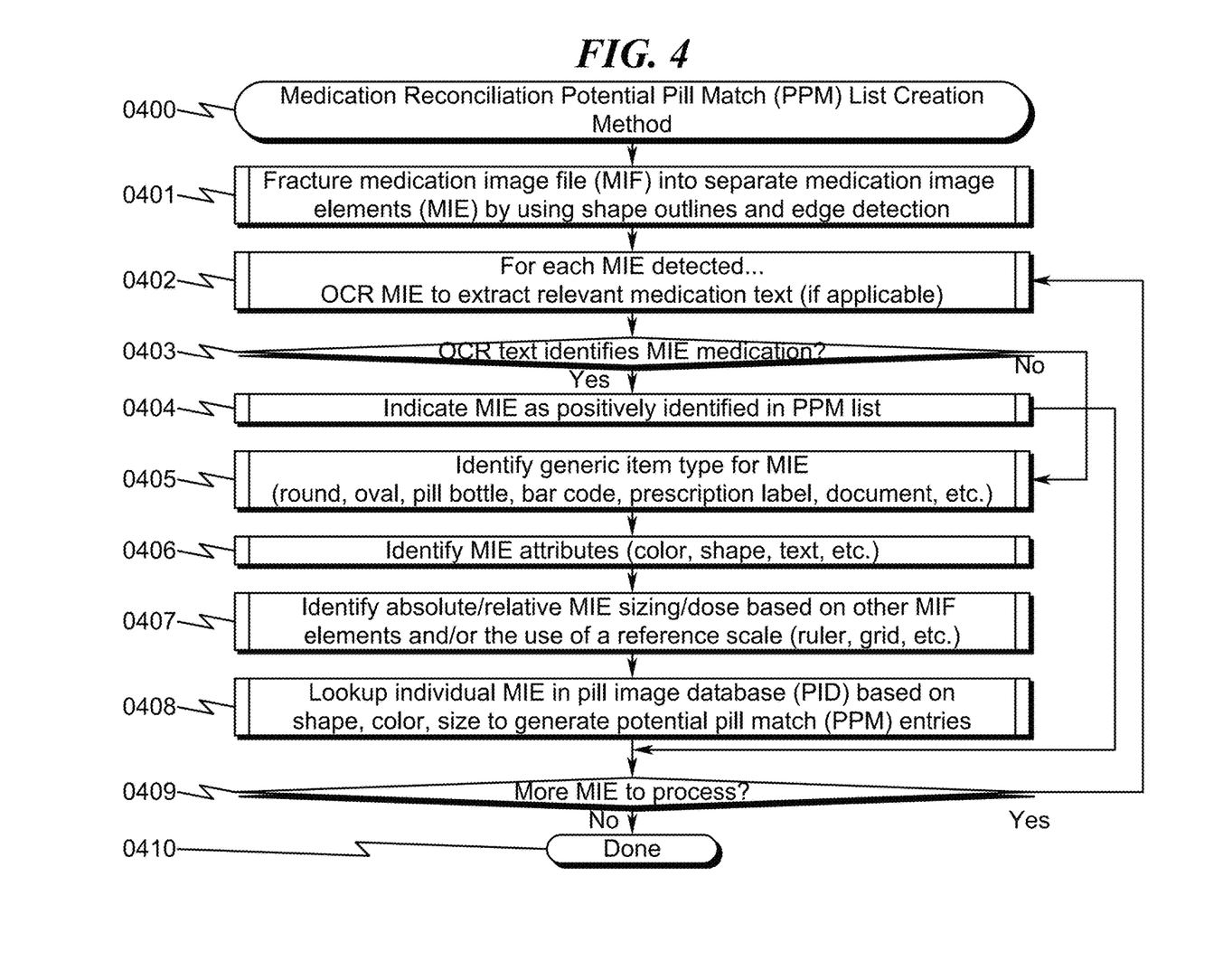
FIG. 4 illustrates a flowchart depicting a preferred exemplary medication reconciliation potential pill match (PPM) list creation method embodiment.

The process of PPM list creation may be generally described as indicated in the flowchart of FIG. 4 (0400) that comprises the following steps:

(1) Fracturing the medication image file (MIF) into separate medication image elements (MIE) by using shape outlines and edge detection (0401);
(2) For each MIE detected start a processing loop by first scanning/imaging the MIE with OCR technology to extract relevant medication text from the MIE (0402);
(3) Determining if the OCR text identifies MIE medication (as in the case of a pill bottle, prescription, bar code, prescription, document, etc.), and if not, proceeding to step (5) (0403);
(4) Indicate MIE as positively identified in the PPM list and proceed to step (9) (0404);
(5) Identify generic item type for the MIE (round, oval, pill bottle, bar code, prescription label, document, etc.) (0405);
(6) Identify the MIE specific attributes (color, shape, text, etc.) (0406);
(7) Identify absolute/relative MIE sizing/dose based on other MIF elements and/or the use of a reference scale (ruler, grid, etc.) (this information may be used to reference known/valid dosing information for medications) (0407);
(8) Lookup individual MIE in the pill image database (PID) based on MIE shape, color, size, dose, etc. to generate potential pill match (PPM) entries for the MIE (0408); and
(9) Determining if there are more MIE items to process within the MIF, and if so, proceeding to step (2) to process the remaining MIEs (0409).

One skilled in the art will recognize that these method steps may be augmented or rearranged without limiting the teachings of the present invention. This general method summary may be augmented by the various elements described herein to produce a wide variety of invention embodiments consistent with this overall design description.

Figure 5:
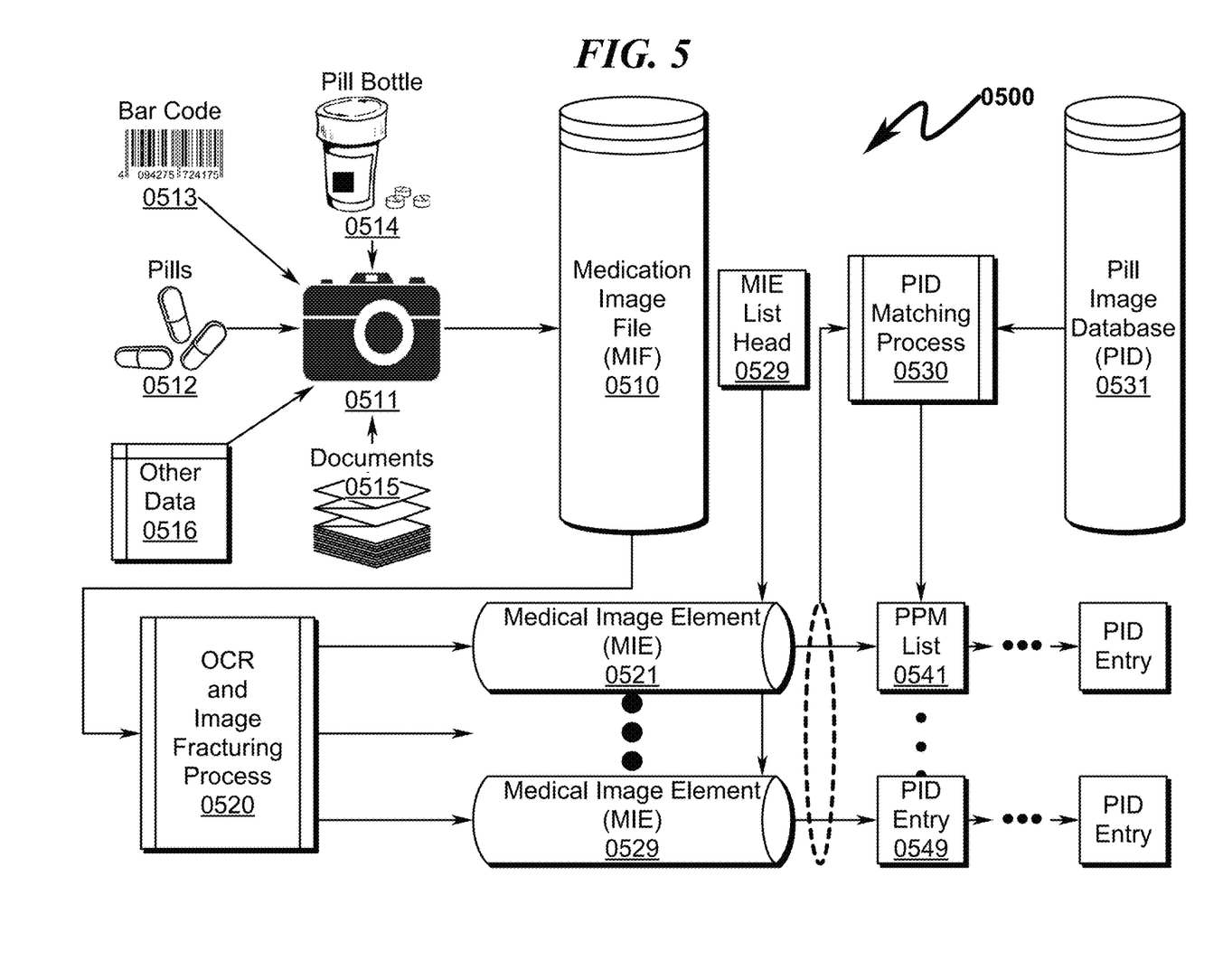
FIG. 5 illustrates a data flow diagram depicting creation of a reconciliation potential pill match (PPM) list.

The data flow in this process is generally illustrated in FIG. 5 (0500) wherein the medication image file (MIF) (0510) is generated via an imaging system (0511) that collects image data from a variety of sources (0512, 0513, 0514, 0515, 0516) that may include actual medications or indicia evidencing the use of medications. The MIF is then processed via an OCR and image fracturing process (0520) as described above to generate the individual MIE files (0521, 0529) that are normally tied together in a linked list having a conventional listhead pointer (0529). These MIE files (0521, 0529) are then compared using a matching process (0530) against a pill image database (PID) (0531) that defines a repository of medication information on the characteristics, names, and other physical criteria associated with wide variety of medications. The result of this matching process (0530) are a series of potential pill match (PPM) lists (0541, 0549) associated with each MIE (0521, 0529) that contain one or more references to the PID as PID entries in the PPM lists (0541, 0549).

Medication Reconciliation PPM List Prioritization Method (0600)

Figure 6:
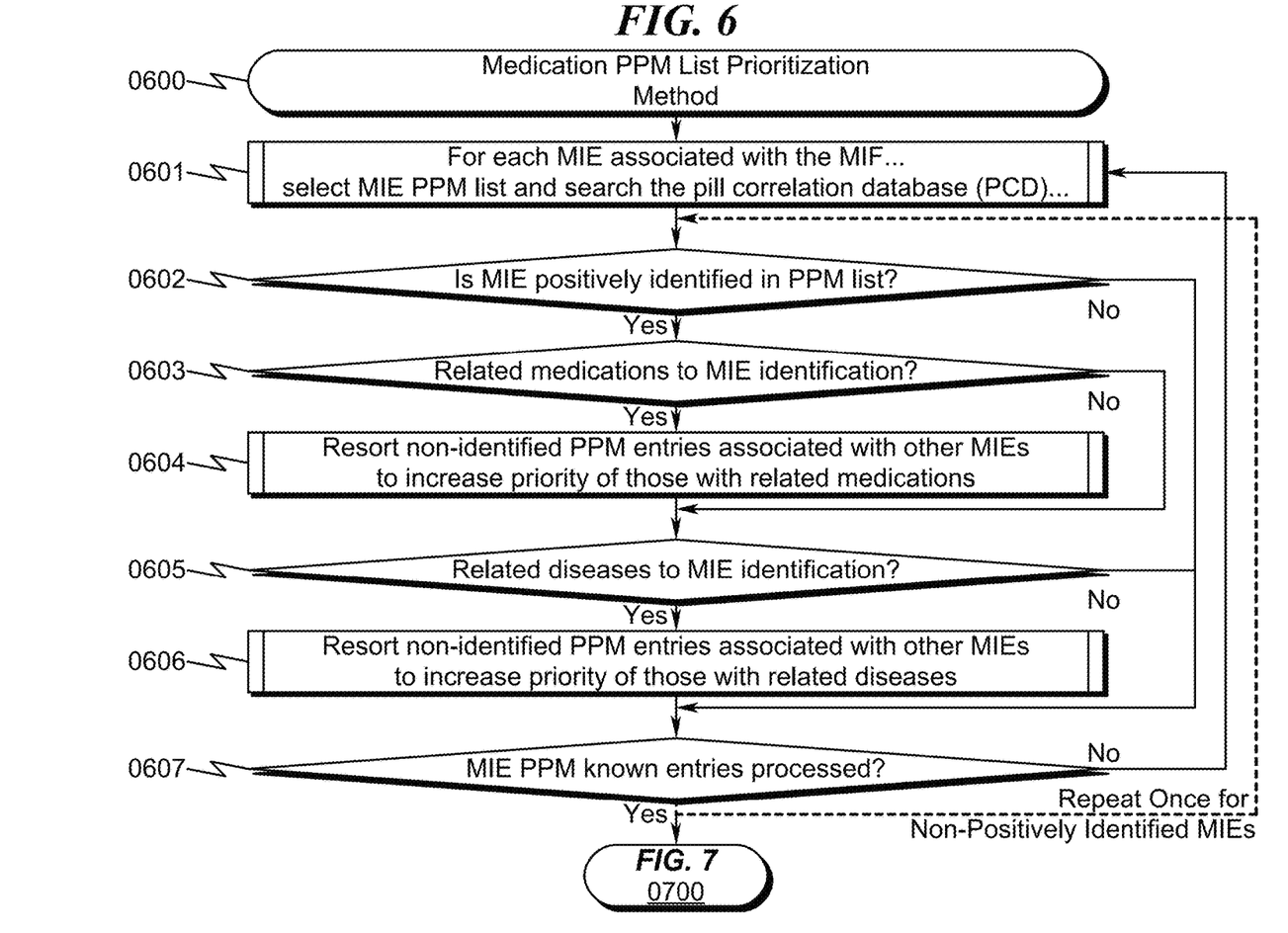
FIG. 6 illustrates a flowchart depicting a preferred exemplary medication reconciliation PPM list prioritization method.

Associated with the exemplary system overview described in above is a medication reconciliation PPM list prioritization method that is used to correlate entries in the PPM list against a pill correlation database (PCD) to rank the possible outcomes for each MIE. Since each MIE may be associated with a number of possible medications (due to similarities in the physical characteristics of the pill as imaged), some methodology is needed to break the deadlock of situations in which a given medication PPM list contains multiple possible match entries. The methodology used in this block inspects each entry in each PPM list to determine if the entry has been positively identified. If so, this information may infer that other related medications or medications associated with related diseases are more probably in the patient medication collection (PMC) and as such can be used to prioritize the PPM list entries, as the related use of a medication increases the probability that the unknown PPM entry order can be deterministically resolved. This methodology is generally described as indicated in the flowchart of FIG. 6 (0600) that comprises the following steps:

(1) For each MIE associated with the MIF, selecting the MIE PPM list and searching the pill correlation database (PCD) for matches to the MIE (0601);
(2) Determining if the MIE is positively identified in PPM list (as in the case of a bar code match, positive pill visual match, OCR medication identification match, etc.), and if not, proceeding to step (7) (0602);

(3) Determining if there are related medications to the MIE identification, and if not, proceeding to step (5) (0603);
(4) Resorting non-identified PPM entries associated with other MIEs to increase the priority of those with related medications (0604);
(5) Determining if there are related diseases to the MIE identification, and if not, proceeding to step (7) (0605);
(6) Resorting non-identified PPM entries associated with other MIEs to increase the priority of those with related diseases (0606); and
(7) Determining if all MIE PPM known entries have been processed, and if not, proceeding to step (1) (note that this loop may optionally be performed one more time by proceeding to step (3) for non-positively identified MIEs to correlate medications and/or diseases among the non-positively identified PPM entries) (0607).

One skilled in the art will recognize that these method steps may be augmented or rearranged without limiting the teachings of the present invention. This general method summary may be augmented by the various elements described herein to produce a wide variety of invention embodiments consistent with this overall design description.

Patient History PPM List Prioritization Method
(0700)

Figure 7:
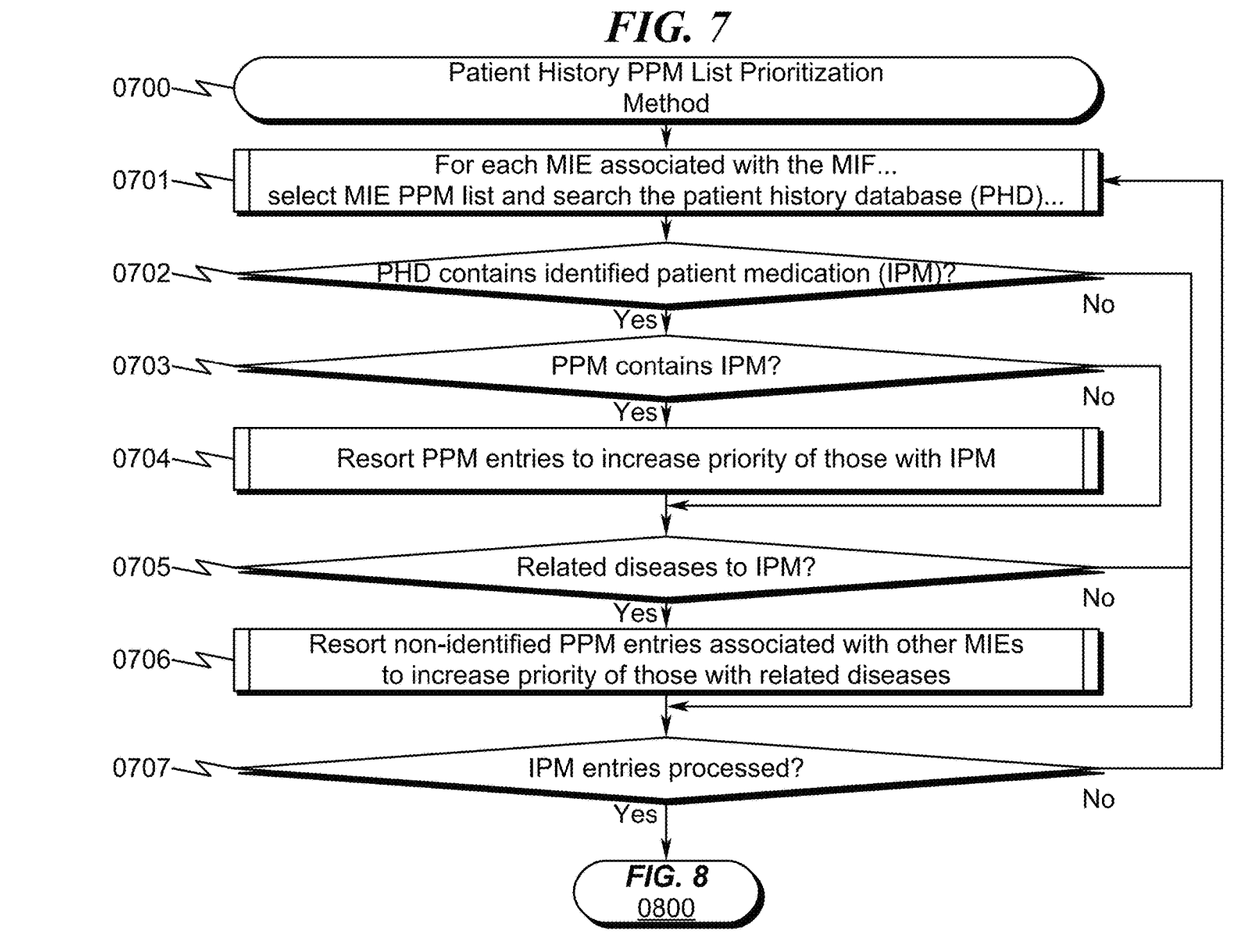
FIG. 7 illustrates a flowchart depicting a preferred exemplary patient history PPM list prioritization method.

Associated with the exemplary system overview described in above is a patient history PPM list prioritization method that is used to correlate entries in the PPM list against a pill correlation database (PCD) to rank the possible outcomes for each MIE. Since each MIE may be associated with a number of possible medications (due to similarities in the physical characteristics of the pill as imaged), some methodology is needed to break the deadlock of situations in which a given medication PPM list contains multiple possible match entries. The methodology used in this block inspects the patient history to determine what medications the patient has used in the past and this information is used to prioritize the PPM list entries, as the prior use of a medication increases the probability that the unknown PPM entry order can be deterministically resolved. This methodology is generally described as indicated in the flowchart of FIG. 7 (0700) that comprises the following steps:
(1) For each MIE associated with the MIF, selecting the MIE PPM list and searching the patient history database (PHD) for medication matches to the MIE (0701);
(2) Determining if the PHD contains an identified patient medication (IPM), and if not, proceeding to step (7) (0702);
(3) Determining if the PPM list contains the IPM, and if not, proceeding to step (5) (0703);
(4) Resorting the PPM entries to increase priority of those with IPM (0704);
(5) Determining if there are related diseases to the IPM, and if not, proceeding to step (7) (0705);
(6) Resorting non-identified PPM entries associated with other MIEs to increase priority of those with related diseases (0706); and
(7) Determining if all IPM entries have been processed, and if not, proceeding to step (1) (0707).

One skilled in the art will recognize that these method steps may be augmented or rearranged without limiting the teachings of the present invention. This general method summary may be augmented by the various elements described herein to produce a wide variety of invention embodiments consistent with this overall design description.

Medical Reading PPM List Prioritization Method
(0800)

Figure 8:
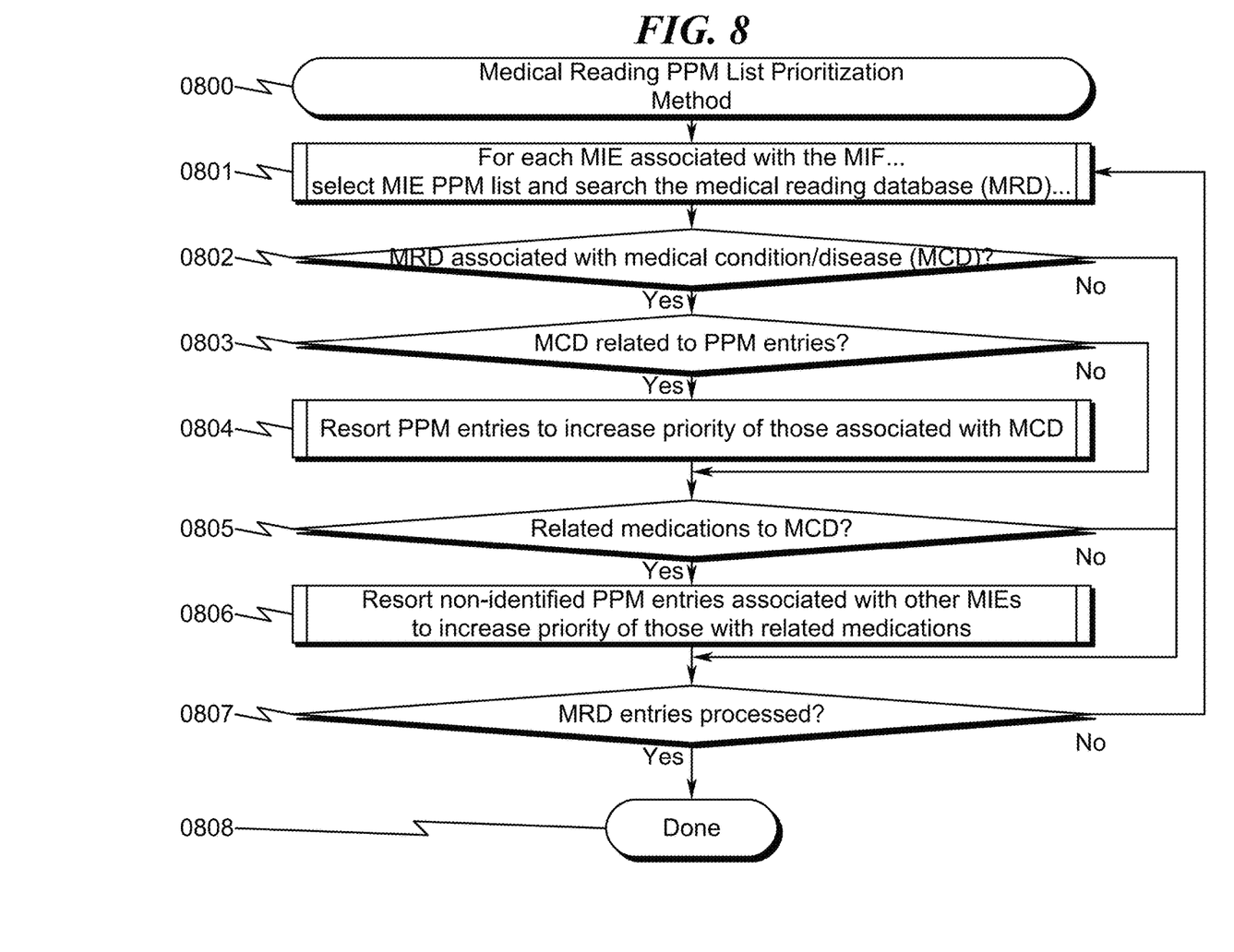
FIG. 8 illustrates a flowchart depicting a preferred exemplary medical reading PPM list prioritization method.

Associated with the exemplary system overview described in above is a medical reading PPM list prioritization method that is used to correlate entries in the PPM list against a pill correlation database (PCD) to rank the possible outcomes for each MIE. Since each MIE may be associated with a number of possible medications (due to similarities in the physical characteristics of the pill as imaged), some methodology is needed to break the deadlock of situations in which a given medication PPM list contains multiple possible match entries. The methodology used in this block inspects real-time patient medical readings that are stored in a medical reading database (MRD) to determine what medications the patient may need that are related to current medical readings and this information is used to prioritize the PPM list entries, as certain medical readings (such as glucose, weight, etc.) increases the probability that the unknown PPM entry order can be deterministically resolved. This methodology is generally described as indicated in the flowchart of FIG. 8 (0800) that comprises the following steps:
(1) For each MIE associated with the MIF, selecting the MIE PPM list and searching the medical reading database (MRD) for medical conditions that may match medication contained in the MIE (the MRD may contain a variety of real-time data obtained from medical instrumentation devices (MIDs) used to collect medical information from the patient and the MID may include one or more patient query/response dialogs (QRD) presented a MUD used to obtain information directly from the patient on their medical condition) (0801);
(2) Determining if the MRD is associated with a medical condition/disease (MCD), and if not, proceeding to step (7) (0802);
(3) Determining if the MCD is related to any PPM entries (by inspection of the pill correlation database (PCD)), and if not, proceeding to step (5) (0803);
(4) Resorting the PPM entries to increase priority of those associated with the MCD (0804);
(5) Determining if there are medications related to MCD, and if not, proceeding to step (7) (0805);
(6) Resorting non-identified PPM entries associated with other MIEs to increase priority of those with related medications (0806); and
(7) Determining if all MRD data entries have been processed, and if not, proceeding to step (1) (0807).

One skilled in the art will recognize that these method steps may be augmented or rearranged without limiting the teachings of the present invention. This general method summary may be augmented by the various elements described herein to produce a wide variety of invention embodiments consistent with this overall design description.

Healthcare Embodiment PHP Integration

The present invention as applied to a healthcare system application context may be summarized as depicted in the HEALTHCARE DELIVERY SYSTEM AND METHOD patent application incorporated by reference herein. In this example a host computer system (HCS) that may incorporate a healthcare web server (HWS) is used to define a patient healthcare plan (PHP) that is used to coordinate the healthcare delivery through a computer network to a patient.

A core concept in this architecture is that the PHP is configurable by healthcare providers from the hospital or other medical facility care management team members to continually drive real-time healthcare to the patient through the MUD. This may include educational materials, real-time interaction with healthcare providers, as well as dynamic display of video based on measured patient medical parameters. One feature of this PHP-driven healthcare delivery system is the potential for directing the patient to perform real-time medication reconciliation as part of the patient care plan. This permits a healthcare provider to trigger a medication reconciliation process on the MUD that is performed by the patient to ensure that the patient medical records are correct and properly updated on initial patient intake. This patient-executed medication reconciliation operation can also be periodically triggered by the PHP on the MUD to ensure that the patient is ingesting the proper medications each day.

Healthcare Method Embodiment Overview

Associated with the exemplary system overview described in above is a medication reconciliation method applied to a healthcare delivery method that comprises the following steps:
 (1) Collecting patient data in real-time within a HIS/EMR infrastructure;
 (2) Allowing definition of a patient healthcare plan (PHP) that coordinates delivery of healthcare to a patient;
 (3) Integrating remote patient monitoring (RPM) data from mobile patient monitoring devices and patient alerts based on execution of the PHP;
 (4) Risk stratifying all active patients to queue prioritized healthcare delivery to patients;
 (5) Displaying risk stratification dashboards in real-time to trigger healthcare provider activity on specific patients;
 (6) Updating/clearing alert status once patient status is improved/modified;
 (7) Allowing the PHP be updated to adjust patient healthcare strategy based on patient alerts; and
 (8) Triggering patient questionnaires/video and/or external interaction on the MUD between the patient and healthcare professionals to force a medication reconciliation audit for the patient to update the patient medical history on the host computer system and then proceeding to step (1).

One skilled in the art will recognize that these method steps may be augmented or rearranged without limiting the teachings of the present invention. This general method summary may be augmented by the various elements described herein to produce a wide variety of invention embodiments consistent with this overall design description.

Note that in step (8) the process may rely heavily on the MUD in order to coordinate the deployment of the PHP to the patient in a directed or autonomous fashion. For example, the PHP may dictate a conference call with a healthcare provider that has access to the patient medical information as well as instructional videos that should be provided to the patient to improve their overall healthcare. This information may be deployed to the MUD for presentation to the patient in a coordinated multi-display multimedia fashion as defined by a user interaction context (UIC). This UIC may be dictated by the PHP and/or MUD to provide for a patient user experience that surpasses that which would normally be available solely from the MUD display context.

Healthcare System Embodiment Overview

The present invention as applied to a healthcare system application context may be summarized as follows and is comprised of four cooperating computer systems as defined by the HIS system, patient remote monitoring system (MUD), caregiver computer system(s), and healthcare web server (HWS) (also termed a host computer system (HCS) in this application). Within this context the system operates to integrate information from the various computer systems as dictated by an overarching patient healthcare plan (PHP) executed as machine instructions read from a computer readable medium that drives information flow between the various computer systems.

A core concept in this architecture is that the PHP is configurable by healthcare providers from the hospital or other medical facility care management team members to continually drive real-time healthcare dashboard status information to authorized healthcare provider recipients based on real-time patient information collected from remote monitoring devices (RMD) (also termed medical instrumentation devices (MID) that drive data to the medical reading database (MRD)) communicating with mobile user devices (MUD) as well as information gathered from patient caregiver interfaces and information collected from real-time data extraction processes operating within the HIS environment. Since current healthcare methodologies isolate the HIS system within the context of a defined hospital healthcare environment, coordination of information among healthcare professionals (including medication reconciliation) after the patient leaves this environment has been problematic. By providing a healthcare web server (HWS) incorporating web portals accessible by the authorized healthcare providers, the system as depicted permits a unified patient healthcare plan (PHP) to act as the driver for the delivery of healthcare to the patient as well as the hub for reporting patient status (including medication reconciliation) to all interested and authorized healthcare professionals servicing the patient.

Within the context of the hospital setting, data is continually collected by the healthcare information system (HIS) computer from a wide variety of data sources such as lab results, patient history information, chart diagnoses, procedures, surgeries, patient vital signs, medication reconciliation, etc. This information normally flows directly from the data sources to the HIS (via manual or automated input) and is collected for deposit within the patient electronic medical record (EMR) database. The present invention inserts a software module (as executed machine instructions read from a computer readable medium) in this HIS context to sniff these data flows and extract information associated with various patients. This real-time patient data is then used as input to the patient healthcare plan (PHP) to drive patient care and also as input to a real-time process configured to risk stratify patients before and after they leave the hospital setting. This permits the care management team or other healthcare providers to have a real-time risk stratification dashboard (that may include real-time medication reconciliation information) that allows at-risk patients to be immediately identified for additional care or modifications to their PHP. This is in contrast to prior art systems that are unable to gather patient data (including medication reconciliation data) across various physician-care boundaries and integrate this information into a coherent risk stratification analysis.

By integrating in-patient information, out-patient information, and information gathered from various healthcare providers, it is possible to immediately address declines in patient health with proactive measures rather than waiting until these conditions reach a critical stage necessitating readmission of the patient to the hospital. It should be noted that medication-related problems associated with poor medication delivery continuity are a high risk factor for hospital readmissions. Therefore, frequent and accurate medication reconciliation is a necessary (but currently absent) component of acceptable patient care procedures. Additionally, within the hospital context, the real-time integration of patient care information permits a real-time risk stratification dashboard to be created that allows hospital and care management staff the ability to allocate their limited resources to patients at the greatest risk of a severe medical event. In this context the monitoring of medication reconciliation by the patient is a significant factor in reducing patient readmissions.

Preferred Embodiment System Summary

The present invention preferred exemplary system embodiment anticipates a wide variety of variations in the basic theme of construction, but can be generalized as a medication reconciliation system comprising:
 (a) host computer system (HSC);
 (b) pill image database (PID);
 (c) pill correlation database (PCD);
 (d) patient history database (PHD);
 (e) medical reading database (MRD);
 (f) mobile user device (MUD); and
 (g) computer communication network (CCN);
 wherein
  the MUD is configured to collect medication image file (MIF) of a patient medication collection (PMC) from a pill source imager (PSI);
  the MUD is configured to transmit the MIF to the HCS;
  the HCS is configured to isolate individual medical image elements (MIE) within the MIF;
  the HCS is configured to compare each of the MIE individually against the PID to generate a potential pill match (PPM) list associated with each MIE;
  the HCS is configured to prioritize each of the PPM using data retrieved from the PCD, the PHD, and the MRD to produce a prioritized medication list (PML) associated with each MIE;
  the HCS is configured to display each of the MIE on a graphical user interface (GUI) and label each of the MIE with the corresponding PML associated with each of the MIE; and
  the HCS is configured to accept input from the GUI to verify the PML associated with each of the MIE to produce a validated medication list (VML).

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a medication reconciliation method comprising:

(1) with a mobile user device (MUD), collecting medication image file (MIF) of a patient medication collection (PMC) from a pill source imager (PSI);
(2) with the MUD, transmitting the MIF to a host computer system (HSC) via a computer communication network (CCN);
(3) with the HCS, isolating individual medical image elements (MIE) within the MIF;
(4) with the HCS, comparing each of the MIE individually against a pill image database (PID) to generate a potential pill match (PPM) list associated with each MIE;
(5) with the HCS, prioritizing each of the PPM using data retrieved from a pill correlation database (PCD), a patient history database (PHD), and a medical reading database (MRD) to produce a prioritized medication list (PML) associated with each MIE;
(6) with the HCS, displaying each of the MIE on a graphical user interface (GUI) and label each of the MIE with the corresponding PML associated with each of the MIE; and
(7) with the HCS, accepting input from the GUI to verify the PML associated with each of the MIE to produce a validated medication list (VML).

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:
 An embodiment wherein the CCN comprises the Internet.
 An embodiment wherein the patient medication collection (PMC) is selected from a group consisting of: pills; capsules; pill bottles; and bar codes.
 An embodiment wherein the MUD is further configured to collect real-time patient medical information (PMI) from a medical instrumentation device (MID) and transfer the PMI in real-time to the MRD.
 An embodiment wherein the MUD is further configured to collect patient medical information (PMI) from a medical instrumentation device (MID) under control of a patient healthcare plan (PHP) executing within the context of the MUD and transfer the PMI to the MRD.
 An embodiment wherein the MUD is further configured to collect patient medical information (PMI) from a medical instrumentation device (MID) and transfer the PMI to the MRD and the MID is selected from a group consisting of: weight scale; pulse oximeter; blood pressure meter; and blood glucose meter; and patient query/response dialog (QRD) presented on the MUD.
 An embodiment wherein the MUD further comprises the PSI.
 An embodiment wherein the HCS is further configured to update the PHD with the VML.
 An embodiment wherein the PCD further comprises a medication group selected from a group consisting of:

medications associated with a specific disease; and medications associated with related diseases.

An embodiment wherein the PHD comprises information on medications taken by the patient.

An embodiment wherein the MIF is collected under control of a patient healthcare plan (PHP) executing within the context of the MUD.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710, 578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method to determine and reconcile medication provided to a patient has been disclosed. The system and method collect a medication image file (MIF) of a patient medication collection (PMC) using a mobile user device (MUD) and pill source imager (PSI). The MUD transmits the MIF to a host computer system (HSC) via a computer communication network (CCN). The HSC isolates individual MIF medication image elements (MIE) and compares each MIE against a pill image database (PID) to generate a potential pill match (PPM) list. The PPM is filtered and prioritized to produce a prioritized medication list (PML) using data from a pill correlation database (PCD), patient history database (PHD), and medical reading database (MRD). The PML describes probable PPM associations with specific known medications. A HCS graphical user interface (GUI) permits validation of each MIE/PML pair to produce a patient reconciled validated medication list (VML).

What is claimed is:

1. A medication reconciliation system comprising:
a host computer system configured to:
receive a medication image file captured with a mobile user device associated with a patient, wherein the medication image file includes an image of pills or capsules;
isolate individual medical image elements within the medication image file, wherein each of the individual medical image elements corresponds to one of the pills or capsules in the medication image file, and the host computer system is configured to, as part of isolating the medical image elements, perform edge detection to identify shape outlines of the pills or capsules within the medication image file;
for each of the medical image elements:
extract a color attribute of the pill or capsule corresponding to the medical image element;
generate a potential pill match list associated with the medical image element based on the shape outline of the pill or capsule corresponding to the medical image element and the color attribute of the pill or capsule corresponding to the medical image element and a set of potential pill matches received by the host computer system;
generate a prioritized medication list for the medical image element based on disease correlation data received by the host computer system and diagnosed disease data of the patient, wherein the prioritized medication list for the medical image element includes a plurality of known pill types within the potential pill match list associated with the medical image element, wherein the disease correlation data indicates a correlation between one or more of the plurality of known pill types in the prioritized medication list for the medical image element and a group of known pill types that are associated with specific or related disease treatments, and wherein each of the known pill types in the prioritized medication list for the medical image element is prioritized in the prioritized medication list for the medical image element based on a probability of the known pill type matching the medical image element; and
display the medical image element on a graphical user interface, the prioritized medication list for the medical image element, and for each of the known pill types in the prioritized medication list for the medical image element, the probability of the known pill type matching the medical image element;
produce a validated medication list based on a received user verification of each of the medical image elements and the prioritized medication lists for the medical image elements; and
for each of the medical image elements, estimate a dose of each of the medical image element by utilizing a reference scale to extract a size attribute of the medical image element.

2. The medication reconciliation system of claim 1, wherein the mobile user device is further configured to collect real-time patient medical information from a medical instrumentation device and migrate the patient medical information in real-time; and
wherein the host computer system is further configured to utilize the real-time patient medical information to produce the potential pill match list.

3. The medication reconciliation system of claim 1, wherein the mobile user device is further configured to collect patient medical information from a medical instrumentation device under control of a patient healthcare plan executing within the context of the mobile user device and migrate the patient medical information.

4. The medication reconciliation system of claim 1, wherein the mobile user device is further configured to collect patient medical information from a medical instrumentation device and transfer the patient medical information to the host computer system, and wherein the medical instrumentation device is selected from a group consisting of:
   a weight scale;
   a pulse oximeter;
   a blood pressure meter;
   a blood glucose meter; and
   a patient query/response dialog (QRD) presented on the mobile user device.

5. The medication reconciliation system of claim 1, wherein the mobile user device further comprises a pill source imager.

6. The medication reconciliation system of claim 1, wherein the host computer system is further configured to migrate the validated medical list.

7. The medication reconciliation system of claim 1, wherein the host computer system is further configured to migrate data describing contraindicated medication combinations.

8. The medication reconciliation system of claim 1, wherein the host computer system is further configured to migrate information on medications taken by the patient.

9. The medication reconciliation system of claim 1, wherein the medical image file is collected under control of a patient healthcare plan executing within the context of the mobile user device.

10. The medication reconciliation system of claim 1, wherein the host computer system is further configured to, for each of the medical image elements, produce the prioritized medication list for the medical image element by prioritizing each potential pill match listed in the potential pill match list associated with the medical image element.

11. The medication reconciliation system of claim 10, wherein the host computer system is configured to assign priority to each potential pill match listed in the potential pill match list associated with the medical image element based on positive identification and association with the color attribute of the pill or capsule corresponding to the medical image element, a shape outline of the pill or capsule corresponding to the medical image element, or a text attribute of the medical image element.

12. A medication reconciliation method comprising:
   receiving, by a host computer system, a medication image file captured with a mobile user device associated with a patient, the medication image file including an image of pills or capsules;
   isolating, by the host computer system, individual medical image elements within the medication image file, wherein each of the individual medical elements corresponds to one of the pills or capsules in the medical image file, wherein isolating the individual image elements within the medical image file comprises performing, by the host computer system, edge detection to identify shape outlines of the pills or capsules within the medication image file;
   for each of the medical image elements:
      extracting, by the host computer system, a color attribute of the pill or capsule corresponding to the medical image element;
      generating, by the host computer system, a potential pill match list associated with the medical image element based on the shape outline of the pill or capsule corresponding to the medical image element and the color attribute of the pill or capsule corresponding to the medical image element and a set of potential pill matches received by the host computer system;
      generating, by the host computer system, a prioritized medication list for the medical image element based on disease correlation data received by the host computer system and diagnosed disease data of the patient, wherein the prioritized medication list includes a plurality of known pill types within the potential pill match list associated with the medical image element, wherein the disease correlation data indicates a correlation between one or more of the plurality of known pill types in the prioritized medication list for the medical image element and a group of known pill types that are associated with specific or related disease treatments, and wherein each of the known pill types in the prioritized medication list for the medical image element is prioritized in the prioritized medication list for the medical image element based on a probability of the known pill type matching with the medical image element;
      displaying, by the host computer system, the medical image element on a graphical user interface (GUI), the prioritized medication list for the medical image element, and, for each of the known pill types in the prioritized medication list for the medical image element, the probability of the known pill type matching the medical image element;
   producing, by the host computer system, a validated medication list based on a received user verification of each of the medical image elements and the prioritized medication lists for the medical image elements; and
   for each of the medical image elements, estimating, by the host computer system, a dose of each of the medical image element by utilizing a reference scale to extract a size attribute of the medical image element.

13. The medication reconciliation method of claim 12, wherein the mobile user device is further configured to collect real-time patient medical information from a medical instrumentation device and migrate the patient medical information in real-time, and wherein the host computer system is further configured to utilize the real-time patient medical information to produce the potential pill match list.

14. The medication reconciliation method of claim 12, wherein the mobile user device is further configured to collect patient medical information from a medical instrumentation device under control of a patient healthcare plan executing within the context of the mobile user device and migrate the patient medical information.

15. The medication reconciliation method of claim 12, wherein the mobile user device is further configured to collect patient medical information from a medical instrumentation device and transfer the patient medical information to the host computer system, and wherein the medical instrumentation device is selected from a group consisting of:
   a weight scale;
   a pulse oximeter;
   a blood pressure meter;

a blood glucose meter; and
a patient query/response dialog presented on the mobile user device.

16. The medication reconciliation method of claim 12, wherein the mobile user device further comprises a photo source imager.

17. The medication reconciliation method of claim 12, wherein the method further comprises, migrating, by the host computer system, is the validated medication list.

18. The medication reconciliation method of claim 12, wherein the method further comprises, migrating, by the host computer system, data describing contraindicated medication combinations.

19. The medication reconciliation method of claim 12, wherein the method further comprises, migrating, by the host computer system, information on medications taken by the patient.

20. The medication reconciliation method of claim 12, wherein the medication image file is collected under control of a patient healthcare plan executing within the context of the mobile user device.

21. The medication reconciliation system of claim 12, wherein the host computer system is further configured to assign priority to each potential pill match listed in the potential pill match list associated with the medical image element based on positive identification and association with a color attribute of the pill or capsule corresponding to the medical image element, the shape outline of the pill or capsule corresponding to the medical image element, or a text attribute of the medical image element.

* * * * *